(12) United States Patent
Kim et al.

(10) Patent No.: US 11,116,404 B2
(45) Date of Patent: Sep. 14, 2021

(54) PATCH GUIDE METHOD AND PROGRAM

(71) Applicant: NEUROPHET Inc., Gwangju (KR)

(72) Inventors: Dong Hyeon Kim, Seoul (KR); Jun Kil Been, Seoul (KR)

(73) Assignee: NEUROPHET Inc., Gwangju (KR)

( * ) Notice: Subject to any disclaimer, the term of this patent is extended or adjusted under 35 U.S.C. 154(b) by 454 days.

(21) Appl. No.: 15/688,005

(22) Filed: Aug. 28, 2017

(65) Prior Publication Data

US 2019/0059732 A1    Feb. 28, 2019

(30) Foreign Application Priority Data

Aug. 25, 2017  (KR) .................. 10-2017-0108056

(51) Int. Cl.
*A61B 5/00*     (2006.01)
*A61B 5/055*    (2006.01)
(Continued)

(52) U.S. Cl.
CPC .......... *A61B 5/0035* (2013.01); *A61B 5/0042* (2013.01); *A61B 5/0077* (2013.01); *A61B 5/055* (2013.01); *G06F 3/14* (2013.01); *G06F 3/147* (2013.01); *G06K 9/00214* (2013.01); *G06K 9/00248* (2013.01); *G06T 7/0012* (2013.01); *G06T 7/11* (2017.01); *G06T 7/33* (2017.01); *G06T 7/55* (2017.01); *G06T 15/205* (2013.01); *G06T 17/20* (2013.01); *A61B 5/369* (2021.01); *A61B 5/7264* (2013.01);
(Continued)

(58) Field of Classification Search
None
See application file for complete search history.

(56) References Cited

U.S. PATENT DOCUMENTS 10,029,093  B2 *  7/2018  Xiao ................. A61N 5/02
2005/0054910 A1 *  3/2005  Tremblay ........... A61B 5/055
                                                    600/411
(Continued)

FOREIGN PATENT DOCUMENTS

CN       106345062 B  *  1/2018
EP       2561810 A1      2/2013
(Continued)

OTHER PUBLICATIONS

An Office Action mailed by the Japan Patent Office dated Nov. 24, 2020, in Japan Patent Application No. 2020-532529, which is related to the present application.
(Continued)

*Primary Examiner* — Pascal M Bui Pho
*Assistant Examiner* — Yi-Shan Yang
(74) *Attorney, Agent, or Firm* — Studebaker & Brackett PC

(57) ABSTRACT

Disclosed is a patch guide method including acquiring a 3-dimensional scan model including the head of an object by using a depth camera, by a computer, acquiring a 3-dimensional brain MRI model of the object, matching the scan model and the brain MRI model to acquire a matched model, acquiring an image captured by photographing the head of the object by using the depth camera, and matching one location of the captured image and one location on the matched model.

12 Claims, 20 Drawing Sheets
(13 of 20 Drawing Sheet(s) Filed in Color)

(51) Int. Cl.
*G06T 15/20* (2011.01)
*G06K 9/00* (2006.01)
*G06T 7/00* (2017.01)
*G06T 7/55* (2017.01)
*G06F 3/14* (2006.01)
*G06T 17/20* (2006.01)
*G06T 7/33* (2017.01)
*G06F 3/147* (2006.01)
*G06T 7/11* (2017.01)
*G01R 33/48* (2006.01)
*G01R 33/563* (2006.01)
*A61B 5/369* (2021.01)

(52) U.S. Cl.
CPC ...... *G01R 33/4806* (2013.01); *G01R 33/4808* (2013.01); *G01R 33/56341* (2013.01); *G06K 2209/05* (2013.01); *G06T 2207/10028* (2013.01); *G06T 2207/10088* (2013.01); *G06T 2207/20081* (2013.01); *G06T 2207/20084* (2013.01); *G06T 2207/30016* (2013.01)

(56) References Cited

U.S. PATENT DOCUMENTS

| 2005/0093889 | A1 | 5/2005 | Sauer | |
|---|---|---|---|---|
| 2005/0203380 | A1 | 9/2005 | Sauer | |
| 2010/0036233 | A1 | 2/2010 | Zhu | |
| 2010/0087698 | A1 | 4/2010 | Hoffman | |
| 2011/0201939 | A1* | 8/2011 | Hubschman | G21K 5/10 600/476 |
| 2012/0268119 | A1* | 10/2012 | Abe | G01R 33/3875 324/307 |
| 2013/0176336 | A1* | 7/2013 | Hannula | A61B 5/0042 345/633 |
| 2014/0228905 | A1* | 8/2014 | Bolea | A61F 5/56 607/42 |
| 2014/0294270 | A1* | 10/2014 | Schneider et al. | G06T 7/00 382/131 |
| 2017/0120041 | A1* | 5/2017 | Wenger et al. | A61N 1/04 |
| 2018/0264264 | A1* | 9/2018 | Skorheim | A61M 21/00 |
| 2018/0369601 | A1* | 12/2018 | Saitoh | A61F 2/04 |
| 2019/0231433 | A1* | 8/2019 | Amanatullah | A61B 5/0064 |

FOREIGN PATENT DOCUMENTS

| JP | 2001-170018 A | 6/2001 | |
|---|---|---|---|
| JP | 2002-272704 A | 9/2002 | |
| JP | 6161004 B | 7/2017 | |
| KR | 10-2017-0015928 A | 2/2017 | |
| WO | WO-2013026749 A1 * | 2/2013 | ............ A61B 5/055 |
| WO | 2015122369 A1 | 8/2015 | |
| WO | 2017015739 A1 | 2/2017 | |

OTHER PUBLICATIONS

An Office Action mailed by the Japan Patent Office dated Mar. 23, 2021, in Japan Patent Application No. 2020-532529, which is related to the present application.

An European search opinion mailed by the European Patent Office dated Jul. 29, 2020, in European Patent Application No. 17922343.3, which is related to the present application.

An International Search Repod mailed by the World Intellectual Property Office dated Jul. 2, 2018, in PCT/KR2017/009349, which is related to the present application.

An Office Action mailed by the Korean Intellectual Property Office dated Aug. 20, 2018, in Korean Patent Application No. 10-2017-0108056, which is related to the present application.

* cited by examiner

600

610

700

(a)

(b)

PATCH GUIDE METHOD AND PROGRAM

CROSS-REFERENCE TO RELATED APPLICATIONS

A claim for priority under 35 U.S.C. § 119 is made to Korean Patent Application No. 10-2017-0108056 filed Aug. 25, 2017, in the Korean Intellectual Property Office, the entire contents of which are hereby incorporated by reference.

BACKGROUND

Embodiments of the inventive concept described herein relate to a patch guide method and a program.

An magnetic resonance imaging (MRI) system is a device that acquires an image for a tomographic portion of an object by expressing an intensity of a magnetic resonance (MR) signal for a radio frequency (RF) signal generated by a magnetic field of a specific intensity in contrast. For example, if an RF signal that resonates only specific atomic nuclei (for example, hydrogen atomic nuclei) is instantaneously irradiated after an object is laid in a strong magnetic field and the is stopped, an MR signal is emitted from the specific atomic nuclei, and the MRI system may receive the MR signal and acquire an MR image. The MR signal refers to an RF signal radiated from the object. The intensity of the MR signal may be determined by the concentration of atoms (for example, hydrogen) included in the object, a relaxation time T1, a relaxation time T2, and blood flows.

The MRI system includes features that are different from those of other imaging devices. Unlike the imaging devices, such as a computerized tomography (CT) device, in which acquisition of an image depends on a direction of detection hardware, the MRI system may acquire a 2D image or a 3D volume image oriented toward an arbitrary point. Further, unlike a CT device, an X-ray device, a positron emission tomography (PET) device, and a single photon emission computed tomography (SPECT) device, the MRI system does not expose a radioactive ray to an object and an inspector and may acquire a neurological image, an intravascular image, a musculoskeletal image, and an oncologic image, in which it is important to clearly describe abnormal tissues by acquiring an image having a high soft tissue contrast.

An electrical brain stimulation refers to a method of finally applying a current to a brain by attaching an electrode to an inside and an outside of the head and allowing a current to flow to the electrode. An electrical brain stimulation is a non-invasive treatment method that may be simply performed, and may be widely used to treat various brain diseases according to the location at which a stimulus is applied and the type of the stimulus.

Further, an EEG (electroencephalogram) that may measure an electrical activity according to the activity of the brain of an object is also widely used in the neurological and neuropsychiatric departments.

Both the electrical brain stimulation and the EEG brain wave inspection are non-invasive inspection and treatment methods, and may be simply performed. However, because the brain structures of the brains and the shapes of the heads of people are different, it is difficult to attach a patch to an accurate location to perform a treatment by the doctor, and thus it is required to develop a patch guide method that reflects the shapes of the heads of people.

SUMMARY

The inventive concept provides a patch guide method and a program.

The technical objects of the inventive concept are not limited to the above-mentioned ones, and the other unmentioned technical objects will become apparent to those skilled in the art from the following description.

In accordance with an aspect of the inventive concept, there is provided a patch guide method including acquiring a 3-dimensional scan model including the head of an object by using a depth camera, by a computer, acquiring a 3-dimensional brain MRI model of the object, matching the scan model and the brain MRI model to acquire a matched model, acquiring an image captured by photographing the head of the object by using the depth camera, and matching one location of the captured image and one location on the matched model.

The patch guide method may further include recognizing at least one patch included in the captured image, determining a location of the recognized patch in the captured image, and acquiring a location of the matched model corresponding to the determined location of the patch.

The matching of the scan model and the brain MRI model may include calculating facial features of the scan model and the brain MRI model, and matching the scan model and the brain MRI model by using the facial features of the scan model and the brain MRI model.

The calculating of the facial feature of the scan model may include acquiring a color image and a depth image including the head of the object, calculating the facial feature of the object by using the color image, and calculating a 3-dimensional location of the facial feature of the object by using the depth image.

The patch guide method may further include displaying an image that guides a location of the patch, at which the head of the object is to be attached, in the captured image, and the displaying of the image may include determining a location, at which the patch is to be attached, on the matched model, and displaying a location corresponding to the determined image in the captured image.

The patch guide method may further include recognizing a patch in the captured image, guiding a movement direction of the recognized patch, and determining whether the recognized patch is attached at the determined location.

The acquiring of the 3-dimensional brain MRI model of the object may include acquiring a brain MRI image of the object, and generating a 3-dimensional brain map of the object, by which a delivery process of an electrical stimulus for the brain of the object is simulated, based on properties of a plurality of areas included in the brain MRI image, and the patch guide method may include determining a location of the patch, at which the head of the object is to be attached, by using the 3-dimensional brain map.

The generating of the 3-dimensional brain map may include generating a 3-dimensional solid image constituted by a plurality of meshes, by which a delivery process of an electrical stimulus for the brain of the object is simulated.

The determining of the location of the patch may include acquiring an object of using the patch, simulating a process of delivering an electrical stimulus to the brain of the object according to a location, at which the patch is attached to the head of the object, and determining the location of the patch by using the acquired object and the simulation result.

In accordance with another aspect of the inventive concept, there is provided a computer readable computer program recorded in a recording medium, which is coupled to a computer that is hardware to perform the method.

The other detailed items of the inventive concept are described and illustrated in the specification and the drawings.

BRIEF DESCRIPTION OF THE FIGURES

The patent or application file contains at least one drawing executed in color. Copies of this patent or patent application publication with color drawing(s) will be provided by the Office upon request and payment of the necessary fee.

The above and other objects and features will become apparent from the following description with reference to the following figures, wherein like reference numerals refer to like parts throughout the various figures unless otherwise specified, and wherein.

DETAILED DESCRIPTION

Figure 1:
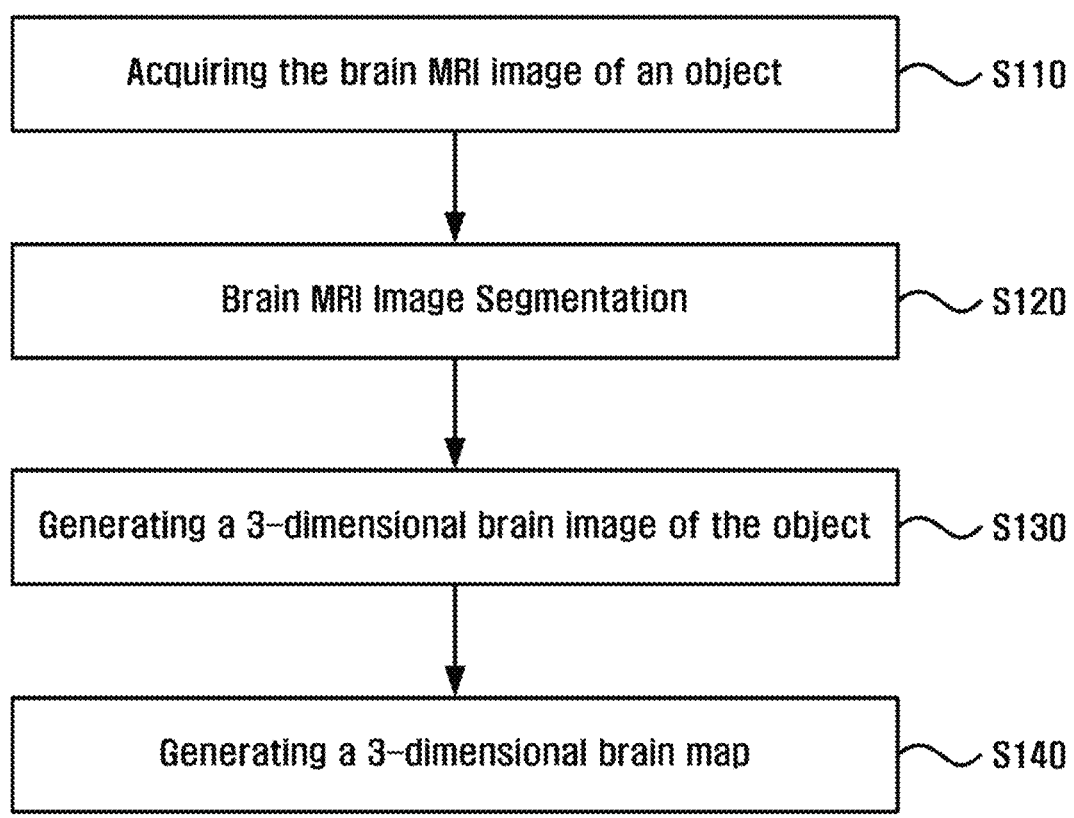
FIG. 1 is a flowchart illustrating a method for generating a 3-dimensional brain map according to an embodiment.

The above and other aspects, features and advantages of the invention will become apparent from the following description of the following embodiments given in conjunction with the accompanying drawings. However, the inventive concept is not limited to the embodiments disclosed below, but may be implemented in various forms. The embodiments of the inventive concept are provided to make the disclosure of the inventive concept complete and fully inform those skilled in the art to which the inventive concept pertains of the scope of the inventive concept.

The terms used herein are provided to describe the embodiments but not to limit the inventive concept. In the specification, the singular forms include plural forms unless particularly mentioned. The terms "comprises" and/or "comprising" used herein does not exclude presence or addition of one or more other elements, in addition to the aforementioned elements. Throughout the specification, the same reference numerals dente the same elements, and "and/or" includes the respective elements and all combinations of the elements. Although "first", "second" and the like are used to describe various elements, the elements are not limited by the terms. The terms are used simply to distinguish one element from other elements. Accordingly, it is apparent that a first element mentioned in the following may be a second element without departing from the spirit of the inventive concept.

Unless otherwise defined, all terms (including technical and scientific terms) used herein have the same meaning as commonly understood by those skilled in the art to which the inventive concept pertains. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein.

The terms "unit" or "module" used herein mean a hardware element such as an FPGA or an ASIC, and the "unit" or "module" performs some functions. However, the "unit" or "module" is not limited to software or hardware. The "unit" or "module" may be constituted in a storage medium that may perform addressing, and may be configured to reproduce one or more processors. Accordingly, as an example, the "unit" or "module" includes elements such as software elements, object-oriented software elements, class elements, and task elements, processes, functions, attributes, procedures, sub-routines, segments of a program code, drivers, firmware, micro-codes, circuits, data, a database, data structures, tables, arrays, and parameters. The elements and the functions provided in the "units" or "modules" may be coupled to a smaller number of elements and the "units" or "modules" or may be separated to additional elements and "units" or "modules".

In the specification, an "object" may include a human being or an animal, or a part of a human being or an animal. For example, the object may include an organ, such as a liver, a heart, a uterus, a brain, a breast, or an abdomen, or a vessel. Further, the "object" may include a phantom. The phantom refers to a material having a volume that is closest to the density of a living thing and the volume of an atomic number, and may include a spherical phantom having a property that is similar to the human body.

Further, in the specification, the "user" is a medical expert and may be a doctor, a nurse, a clinical expert, and a medical image expert, and may be an engineer who repairs a medical device, but is not limited thereto.

Further, in the specification, a "magnetic resonance (MR) image" refers to an image for an object acquired by using a nuclear magnetic resonance principle.

Hereinafter, exemplary embodiments of the inventive concept will be described in detail with reference to the accompanying drawings.

FIG. 1 is a flowchart illustrating a method for generating a 3-dimensional brain map according to an embodiment.

FIG. 1 illustrates operations of the method, which are performed by a computer, in time series. In the specification, a computer is construed to include all computing devices including at least one processor.

In operation S110, the computer acquires a brain MRI image of an object.

In an embodiment, the computer may directly acquire a brain MRI image of an object from an MRI image acquiring device, as a workstation connected to the MRI image acquiring device.

Further, the computer may acquire a brain MRI image of an object from an external server or another computer.

In the disclosed embodiment, a brain MRI image of an object refers to an MRI image that is captured by photographing a head part including a brain of the object. That is, a brain MRI image of an object refers to an MRI image including the skull and the scalp of the object, as well as the brain of the object.

In operation S120, the computer segments (divides) the brain MRI image acquired in operation S110 into a plurality of areas.

In an embodiment, the computer segments the brain MRI image acquired in operation S110 for respective sections of the brain MRI image. Although the computer, for example, may segment the brain MRI image acquired in operation S110 into sections corresponding to a white matter, a gray matter, cerebrospinal fluid, a skull, and scalp, the types of segmenting the brain MRI image are not limited thereto.

In an embodiment, the computer acquires the segmented brain MRI image of the object by inputting the brain MRI image of the object to a model that is learned by using a plurality of processed brain MRI images.

In an embodiment, the processed brain MRI images are images in which a plurality of images included in the brain MRI image are labeled. Further, the learned model is a model that receives a brain MRI Image and outputs the segmented brain MRI image.

In an embodiment, the learned model refers to a model that is learned by using machine learning, and particularly may refer to a model that is learned by using deep learning.

In an embodiment, although the learned model may be a model including one or more batch normalization layers, activation layers, and convolution layers, the inventive concept is not limited thereto.

In an embodiment, the learned model may include a horizontal pipeline including a plurality of blocks that extract high level characteristics from low level characteristics of the MRI image and a vertical pipeline that collects the extracted characteristics from the horizontal pipeline to perform segmentation, in order to perform segmentation of the MRI image, the screen quality of which is relatively low.

Figure 3:
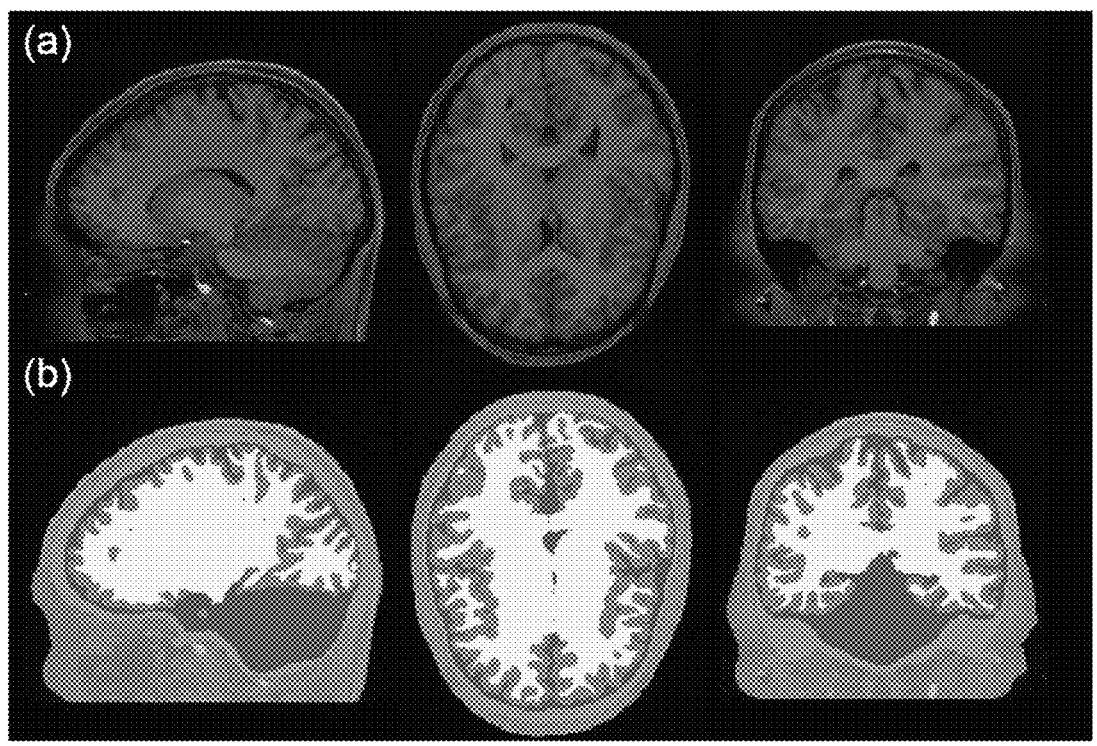
FIG. 3 is a view illustrating a result of segmenting brain MRI images.

Referring to FIG. 3, result images (b) of brain MRI images 300 obtained by performing segmentation on original brain MRI images (a) of the brain MRI images 300 are illustrated.

In an embodiment, the computer performs post-processing of the segmentation result.

In an embodiment, the computer performs connected component-based noise rejection. The connected component-based noise rejection method is used to improve the result of the performed segmentation by using a convolution neutral network (CNN).

Figure 4:
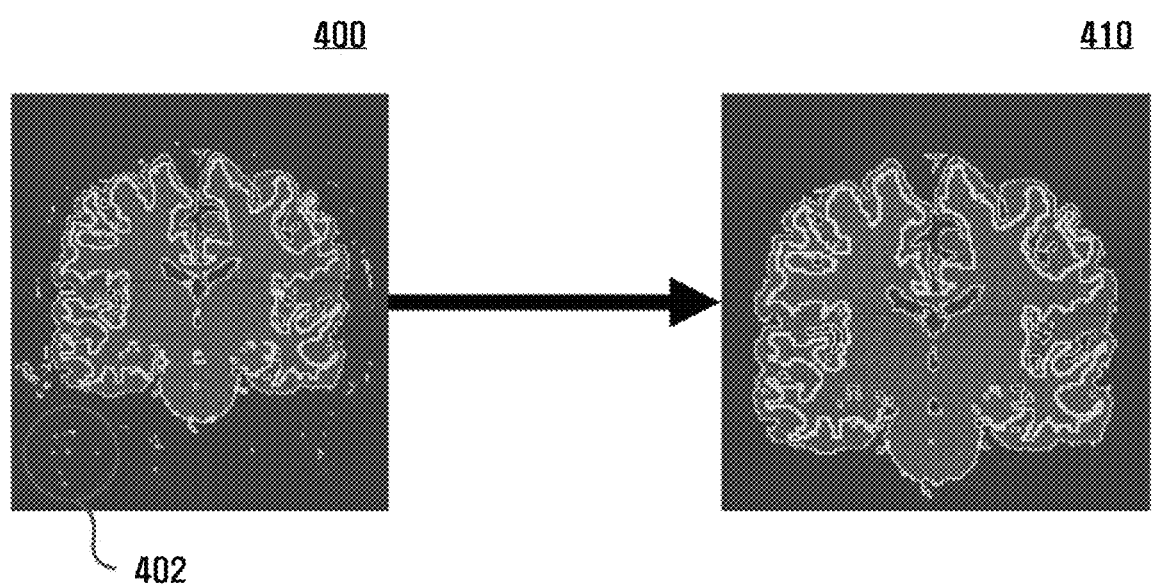
FIG. 4 is a view illustrating an example of a computer performs connected component-based noise rejection method.

Referring to FIG. 4, an example of the connected component-based noise rejection method is illustrated.

The computer acquires an improved segmentation image 410 by removing the remaining components 402 except for a connected component that is the largest chuck of the segmentation image 400.

In an embodiment, the computer performs hole rejection. The hole rejection is used to remove a hole that is one of the errors of the convolution neutral network-based segmentation.

Figure 5:
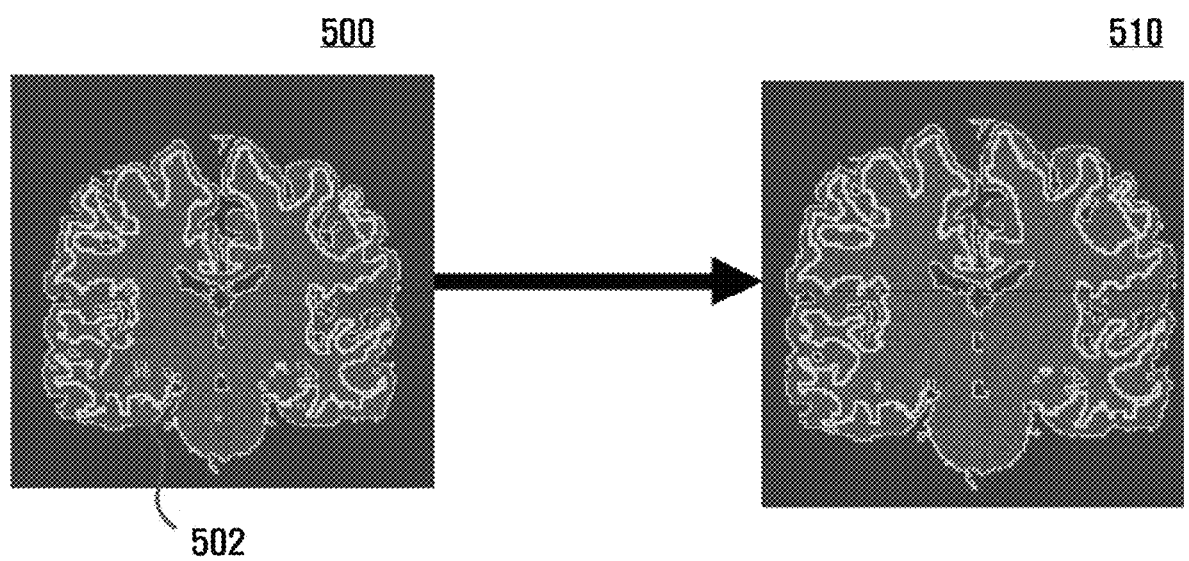
FIG. 5 is a view illustrating an example of a post-processing method using hole rejection.

Referring to FIG. 5, an example of a post-processing method using hole rejection is illustrated.

The computer acquires an improved segmentation image 510 by removing at least a portion of the hole 502 included in the segmentation image 500.

In operation S130, the computer generates a 3-dimensional brain image of an object including a plurality of segmented areas by using the segmented brain MRI image of the object.

Figure 6:
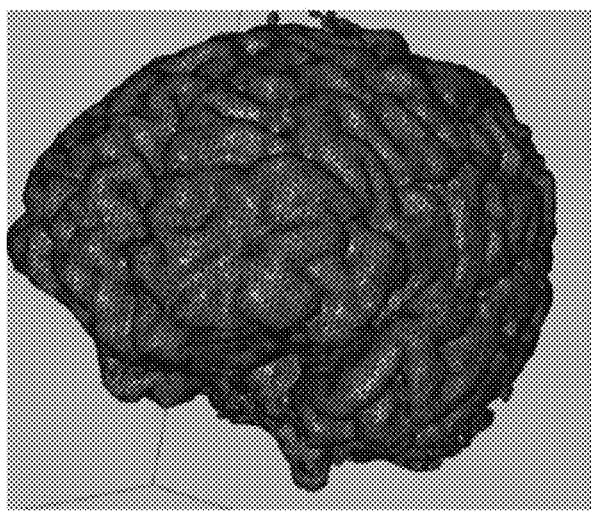
FIG. 6 is a view illustrating an example of a 3-dimensional brain image generated from a brain MRI image of an object.
Figure 6:
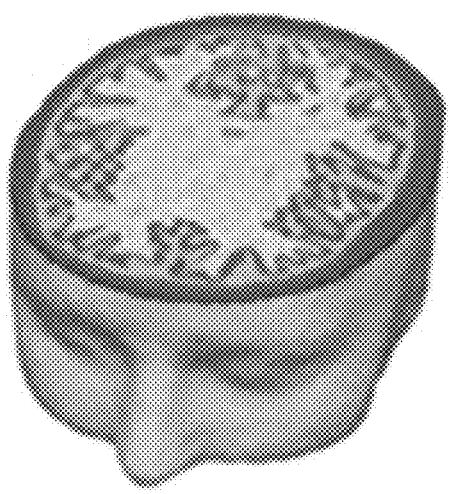

Referring to FIG. 6, a 3-dimensional brain image 600 generated from the brain MRI image of the object is illustrated.

Further, an example of generating a segmented 3-dimensional brain image 610 of the object, from a segmented 2-dimensional bran MRI image of the object is illustrated in FIG. 6.

In operation S140, the computer generates a 3-dimensional brain map that may simulate a process of delivering an electrical stimulus to a brain of an object, based on the properties of a plurality of images included in the 3-dimensional brain image generated in operation S130.

A detailed method of generating a 3-dimensional brain map of the object and performing simulation by using the generated brain map will be described with reference to FIG. 2.

Figure 2:
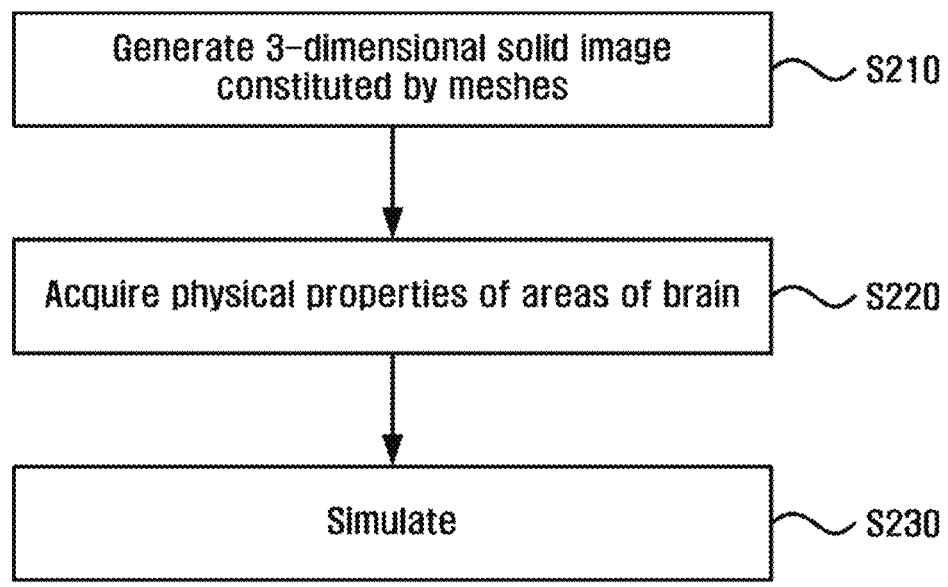
FIG. 2 is a flowchart illustrating a method for generating a 3-dimensional brain map and performing simulation according to an embodiment.

FIG. 2 is a flowchart illustrating a method for generating a 3-dimensional brain map and performing simulation according to an embodiment.

The method of FIG. 2 corresponds to an embodiment of the method of FIG. 1. Accordingly, the contents described in relation to FIG. 1 are also applied to the method of FIG. 2 even though they correspond to the contents omitted in relation to FIG. 2.

In operation S210, the computer generates a 3-dimensional solid image including a plurality of meshes that may simulate a process of delivering an electrical stimulus to the brain of the object, by using the 3-dimensional brain image of the object.

In an embodiment, the computer generates a 3-dimensional solid image including a plurality of surface meshes including triangles or quadrangles.

In an embodiment, the computer generates a 3-dimensional solid image including a plurality of surface meshes including tetrahedrons or octahedrons.

The type of the meshes constituting the 3-dimensional solid image may be differently set according to the purpose of simulation.

In operation S220, the computer acquires physical characteristics of the plurality of areas for simulating current flows according to an electrical stimulus to the brain of the object.

In an embodiment, the physical characteristics acquired in operation S220 include at least one of isotropic electrical conductivities and anisotropic electrical conductivities of the plurality of segmented areas.

In an embodiment, the isotropic electrical conductivities may be acquired by allocating electrical conductivities, which have been known through experiments, to the respective segmented areas.

For example, the electrical conductivities known for the respective areas of the brain are as in Table 1.

TABLE 1

| Area | Electrical conductivity (S/m) |
| --- | --- |
| White matter | 0.126 |
| Gray matter | 0.276 |
| Cerebrospinal fluid | 1.65 |
| Skull | 0.01 |
| Scalp | 0.465 |

The anisotropic electrical conductivities realize the anisotropy of the white matter fibers in the white matter of the brain.

In an embodiment, the anisotropic electrical conductivity is acquired from a conductive tensor image for the brain of the object.

For example, the computer acquires a conductive tensor image for the brain of the object from the brain MRI image of the object, and acquires the anisotropic electrical conductivities of the plurality of segmented areas by using the acquired conductive tensor image.

In another embodiment, the brain MRI image of the object includes a diffusion tensor image, and the computer acquires the anisotropic electrical conductivities of the plurality of segmented areas by using the diffusion tensor image of the object.

Figure 7:
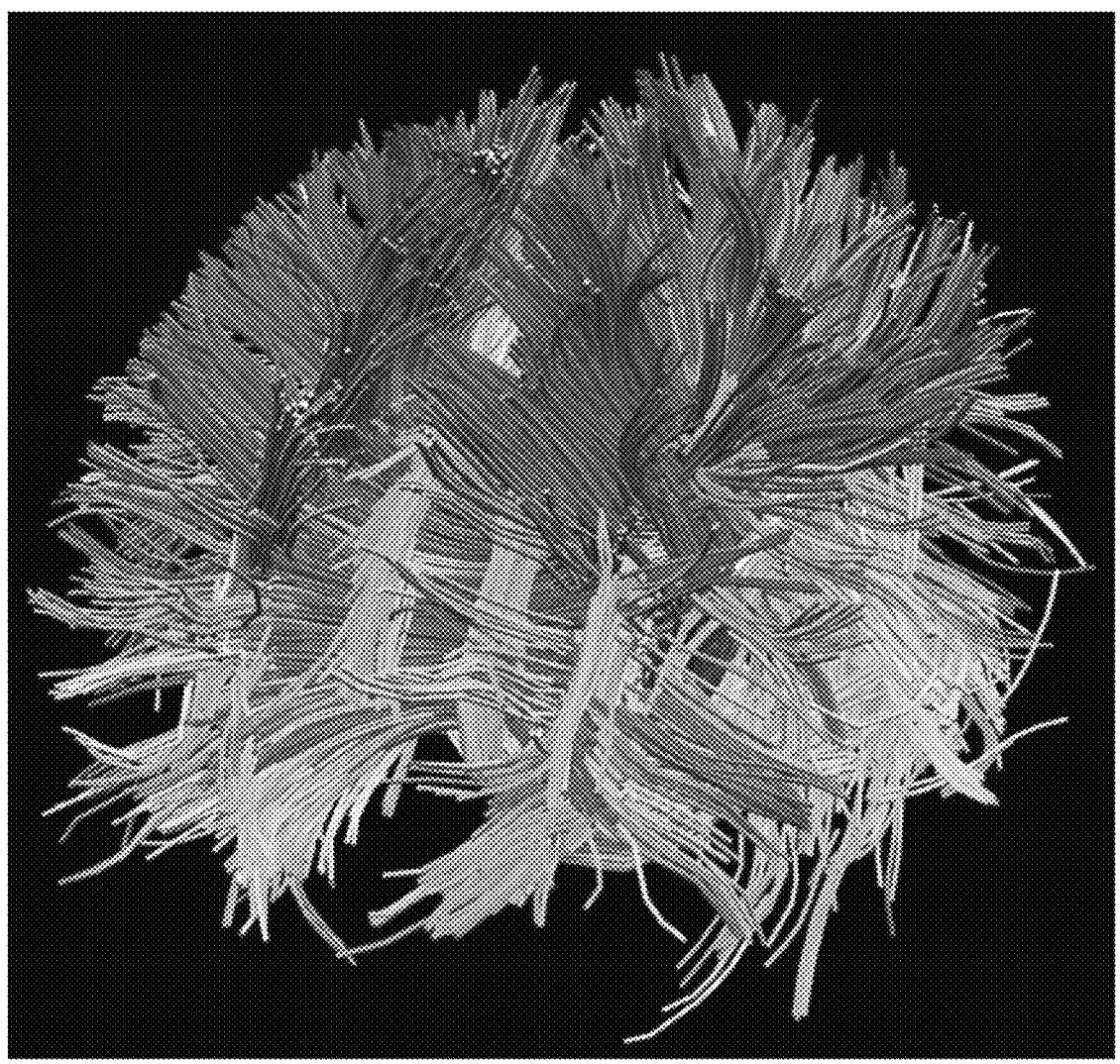
FIG. 7 is a view illustrating an example of a diffusion tensor image.

Referring to FIG. 7, an example of the diffusion tensor image 700 is illustrated.

An eigenvector of the diffusion tensor image is known to coincide with an eigenvector of a conductive tensor, and the computer may acquire an anisotropic electrical conductivity according to a direction of a neutral fiber included in the diffusion tensor image. For example, the direction of the neutral fiber has a high electrical conductivity and a direction that is perpendicular to the neutral fiber has a low electrical conductivity.

In operation S230, the computer simulates a state in which a specific electrical stimulus propagates in the brain of the object when the specific electrical stimulus is applied to one point of the head of the object, by using a 3-dimensional brain map.

In an embodiment, the computer simulates a state in which the electrical stimulus propagates in the brain of the object by using the mesh image acquired in operation S210 and the physical properties acquired in operation S220.

Figure 8:
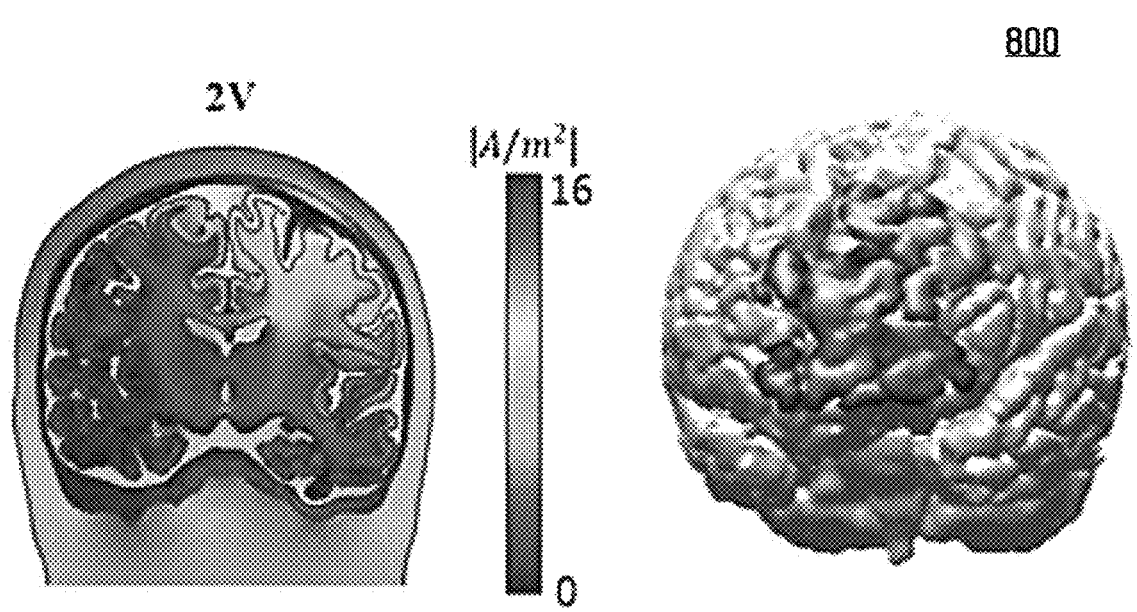
FIG. 8 is a view illustrating an example of a simulation result.

Referring to FIG. 8, an example of a simulation result is illustrated.

An electrical stimulus that may be applied to the head of an object may include at least one of a magnetic field, an electric field, and a current, and when a magnetic field is applied to the head of the object, a current induced by the magnetic field may propagate to the brain of the object.

In an embodiment, the computer acquires a target stimulus point, to which an electrical stimulus is to be applied in the brain of the object. The computer acquires a location, to which an electrical stimulus is to be applied to the head of the object, to apply an electrical stimulus to the target stimulus point, by using a 3-dimensional brain map of the object.

For example, the computer may acquire a recommended path for delivering an electrical stimulus from the scalp of the object to the target stimulus point by using the 3-dimensional brain map of the object, and may acquire a location, at which an electrical stimulus is to be applied to the head of the object, from the recommended path.

A method for calculating and providing a location and a direction for applying an electrical stimulus to the brain of the object by the computer will be described below.

Figure 9:
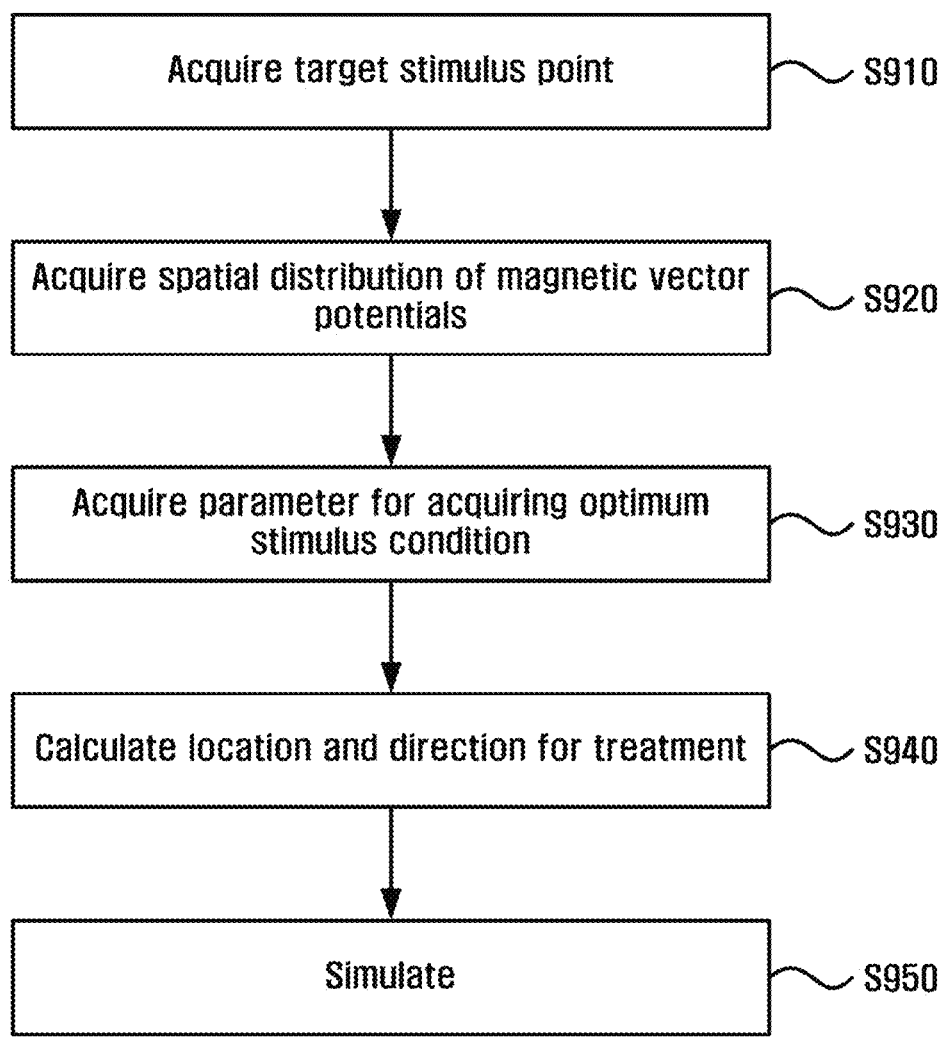
FIG. 9 is a flowchart illustrating a TMS stimulus method according to an embodiment.

FIG. 9 is a flowchart illustrating a transcranial magnetic stimulation (TMS) stimulus navigation method according to an embodiment.

FIG. 9 illustrates operations of the TMS stimulus navigation method, which are performed by a computer, in time series.

Figure 10:
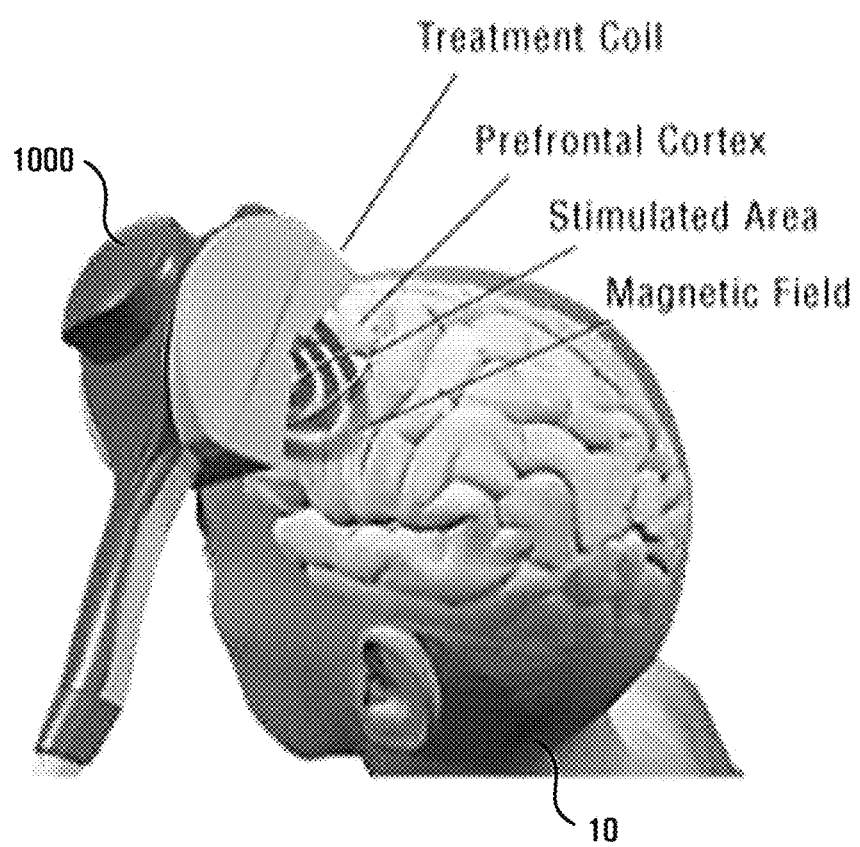
FIG. 10 is a view illustrating an example of a TMS treatment method.

Referring to FIG. 10, an example of a TMS treatment method is illustrated.

The TMS is a treatment method that stimulates a specific portion of a brain of an object by using an electric field induced in the brain with a magnetic field generated by a treatment coil 1000, by allowing the coil 1000 to approach one side surface of the head of the object 10.

The intensities and forms of the magnetic fields generated around the treatment coil 100 will be different according to the shape of the treatment coil 1000, and the forms in which the electrical signals propagate will be different according to the forms of the head and the brain of the object 10.

Accordingly, according to the disclosed embodiment, a stimulus point based on the type of the coil 1000 is calculated and provided, and a simulation result according to the forms of the head and the brain of the object 10 is provided.

In operation S910, the computer acquires a target stimulus point, to which an electrical stimulus is to be applied in the brain of the object.

The target stimulus point is selected based on a clinical or theoretical basis according to a disease that is to be treated. In an embodiment, the target stimulus point is indicated by using a 3-dimensional brain image or a 3-dimensional brain map of the object generated by the disclosed embodiment.

In operation S920, information on a spatial distribution of magnetic vector potentials of the TMS treatment coil is acquired.

In an embodiment, the information on the spatial distribution includes information that is obtained by visualizing a magnetic vector potential by using a magnetic dipole according to the shape of the treatment coil.

Figure 12:
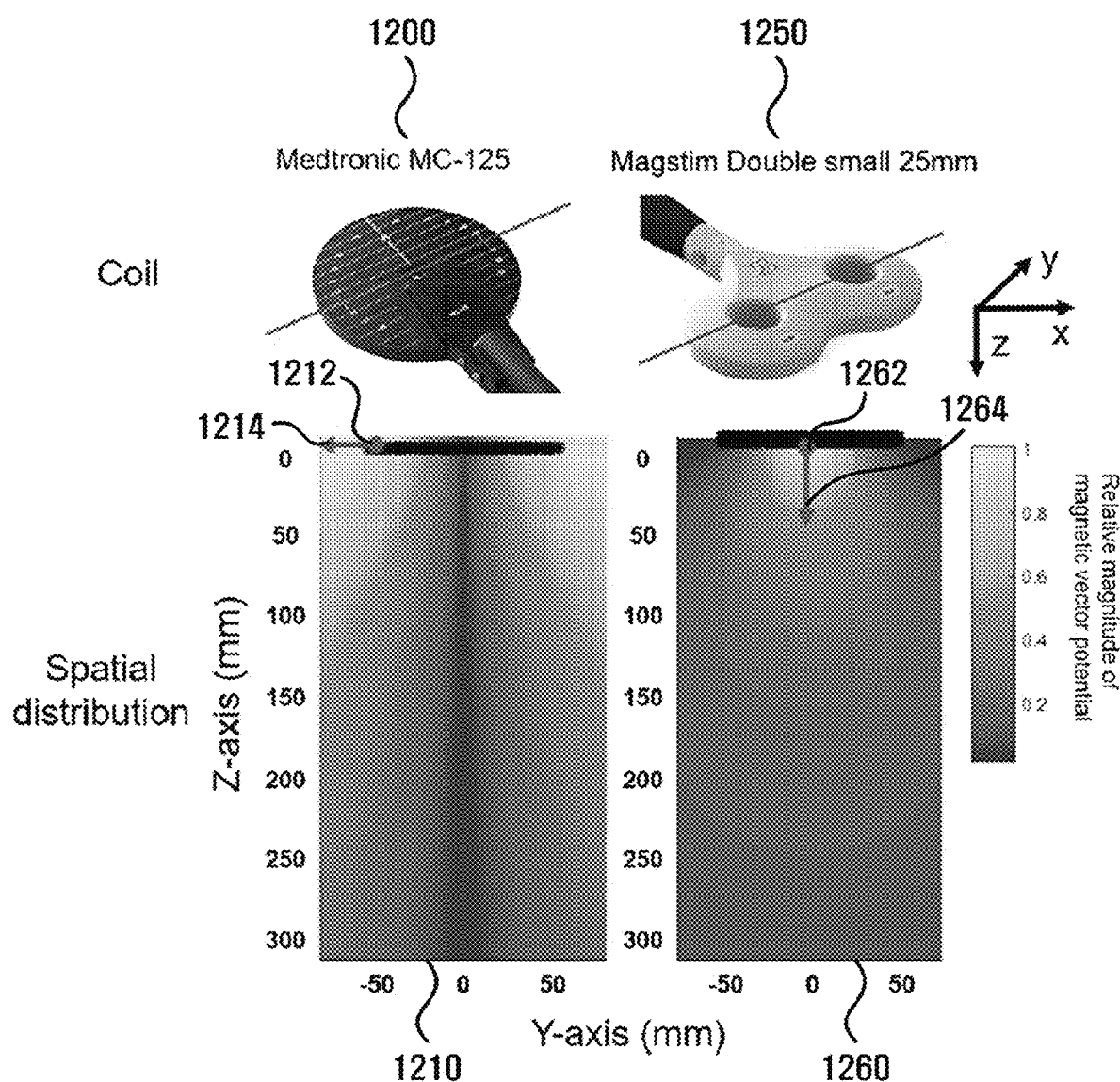
FIG. 12 is a view illustrating information obtained by visualizing a magnetic vector potential according to the type of a treatment coil.

Referring to FIG. 12, information 1210 and 1260 that is obtained by visualizing a magnetic vector potential according to the types of the treatment coils 1200 and 1250.

In operation S930, the computer acquires one or more parameters for acquiring an optimal stimulus condition for the target stimulus point acquired in operation S910 from the spatial distribution acquired in operation S920.

In an embodiment, the optimal stimulus condition for the target stimulus point refers to a condition in which the intensity of the magnetic field applied to the target stimulus point is maximized by the treatment coil.

Figure 11:
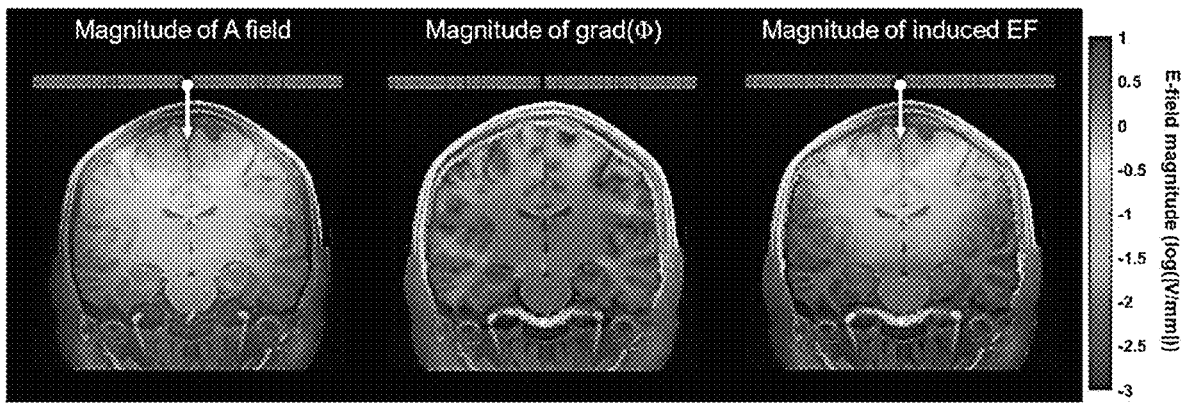
FIG. 11 is a view illustrating a relationship between a magnetic field and an electric field applied to a brain of an object.
Figure 11:
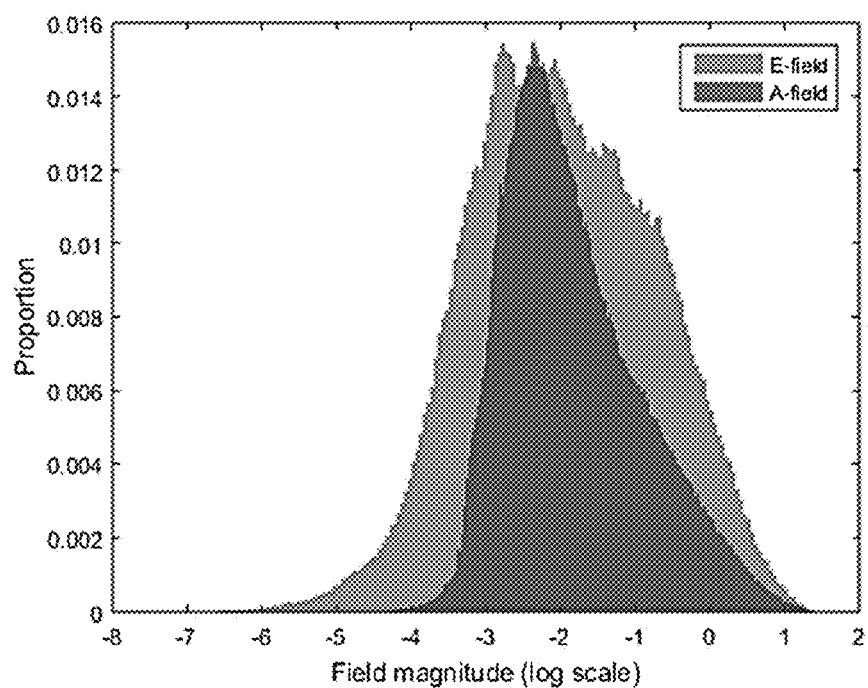

Referring to FIG. 11, a relationship between the magnetic field and the electric field applied to the brain of the object is illustrated.

Referring to simulation images (a) of a relationship diagram 1100 of FIG. 11, images that are obtained by visualizing the intensity of a magnetic field applied to the brain of the object, the intensity of a gradient (potential), and the intensity of an electric field induced by a magnetic field are illustrated. The intensity of the electric field applied to the brain of the object may be calculated by adding the magnetic field and the gradient applied to the brain of the object.

Referring to a graph (b) of the relationship diagram 1100 of FIG. 11, a correlation of a magnetic field applied to the brain of the object and an electric field induced by the magnetic field is illustrated.

According to the graph (b), it can be seen that a stronger electric field is induced in the brain of the object as a stronger magnetic field is applied to the brain of the object.

Accordingly, it can be seen that the optimal stimulus condition for the target stimulus point is determined such that the intensity of the magnetic field applied to the target stimulus point by the treatment coil is maximized.

In an embodiment, the parameter acquired by the computer includes an optimal point having the highest magnetic vector potential value in a spatial distribution of a magnetic vector potential induced by the coil.

Further, the parameter acquired by the computer includes an optimal vector that is a normal vector, of which a product of the normal vector and the gradient is minimized, of the normal vectors, of which the optimal points becomes start points.

Referring to FIG. 12, the optimal points 1212 and 1262 and the optimal vectors 1214 and 1264 of the magnetic vector potentials 1210 and 1250 are illustrated.

The optimal point f and the optimal vector v are calculated by Equations 1 and 2.

$$\max_{x,y,z} f(x, y, z) \quad \text{[Equation 1]}$$

$$\min_{i,j,k} \nabla f(\overline{x}, \overline{y}, \overline{z})^T v(i, j, k) \quad \text{[Equation 2]}$$

In Equation 2, $\nabla f(\overline{x}, \overline{y}, \overline{z})$ are values that are obtained by differentiating f used when the optimal point is defined at $\overline{x}$, $\overline{y}$, $\overline{z}$, and v(i, j, k) refer to normal vectors in the direction of (i, j, k).

In operation S940, a location and a direction of the coil that satisfies an optimal stimulus condition for the target stimulus point acquired in operation S910, by using the parameter acquired in operation S930.

In an embodiment, the operation of calculating the location and the direction of the coil includes an operation of calculating the location and the direction of the coil that allows the target stimulus point to approach an optimal vector from an optimal point most.

Figure 13:
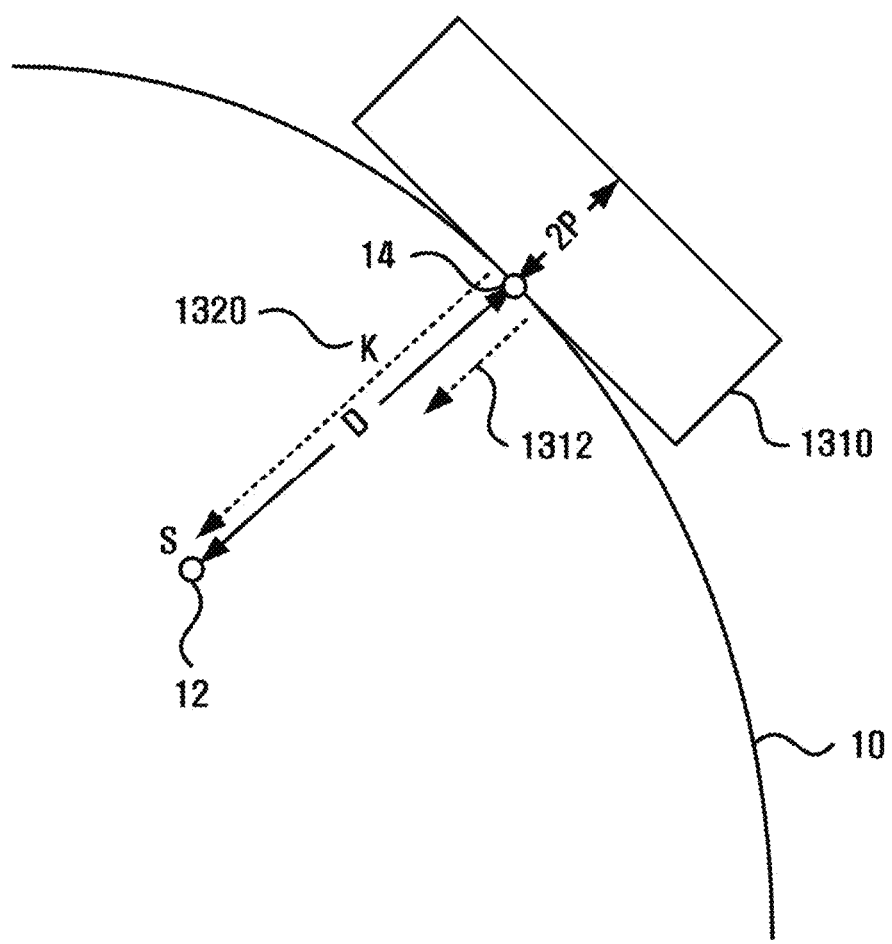
FIG. 13 is a view illustrating an example of a method of calculating a location and a direction of a coil.

Referring to FIG. 13, an example of a method for calculating a location and a direction of the coil is illustrated.

If the object 10 and a target stimulus point (S, 12) of the object are acquired, the computer determines one point 14 on scalp that is closest from the target stimulus point 12.

Then, it is assumed that a distance between the target stimulus point 12 and one point 14 on the scalp that is closest to the target stimulus point 12 is d and a vector, of which a start point is the point 14 and of which an end point 12 is the target stimulus point 12, is K. Further, a thickness of the coil 1310 is 2P.

The computer generates and applies a matrix as in Equation 3 in which the vector K 1320 and the optimal vector 1312 of the coil 1310 are arranged.

$$R_x(\theta) = \begin{bmatrix} 1 & 0 & 0 \\ 0 & \cos\theta & -\sin\theta \\ 0 & \sin\theta & \cos\theta \end{bmatrix} \quad \text{[Equation 3]}$$

-continued $$R_y(\theta) = \begin{bmatrix} \cos\theta & 0 & \sin\theta \\ 0 & 1 & 0 \\ -\sin\theta & 0 & \cos\theta \end{bmatrix}$$

$$R_z(\theta) = \begin{bmatrix} \cos\theta & -\sin\theta & 0 \\ \sin\theta & \cos\theta & 0 \\ 0 & 0 & 1 \end{bmatrix}$$

Accordingly, the location of the coil is calculated as in Equation 4.

$$\text{Loc}_{\text{dipole}} = S + K*(D+P) \quad \text{[Equation 4]}$$

In operation S950, when the treatment coil is located at the location calculated in operation S940 in the direction calculated in operation S950, the computer simulates a state in which an electrical stimulus induced from the magnetic field of the treatment coil propagates in the brain of the object.

In an embodiment, the computer performs simulation by using the 3-dimensional brain map generated according to the methods of FIGS. 1 and 2.

For example, the computer may generate a brain MRI image of the object, and may generate a 3-dimensional brain map that may simulate a delivery process of an electrical stimulus for the brain of the object based on the properties of the plurality of areas included in the acquired brain MRI image.

The computer simulates a state in which an electrical stimulus by the coil propagates in the brain of the object by using a 3-dimensional brain map.

Further, the 3-dimensional map may include a 3-dimensional solid image including a plurality of meshes by which a delivery process of an electrical stimulus for the brain of the object may be simulated.

In an embodiment, the computer visualizes a state in which an electrical stimulus induced from a magnetic field of a treatment coil by using a 3-dimensional solid image.

Figure 14:
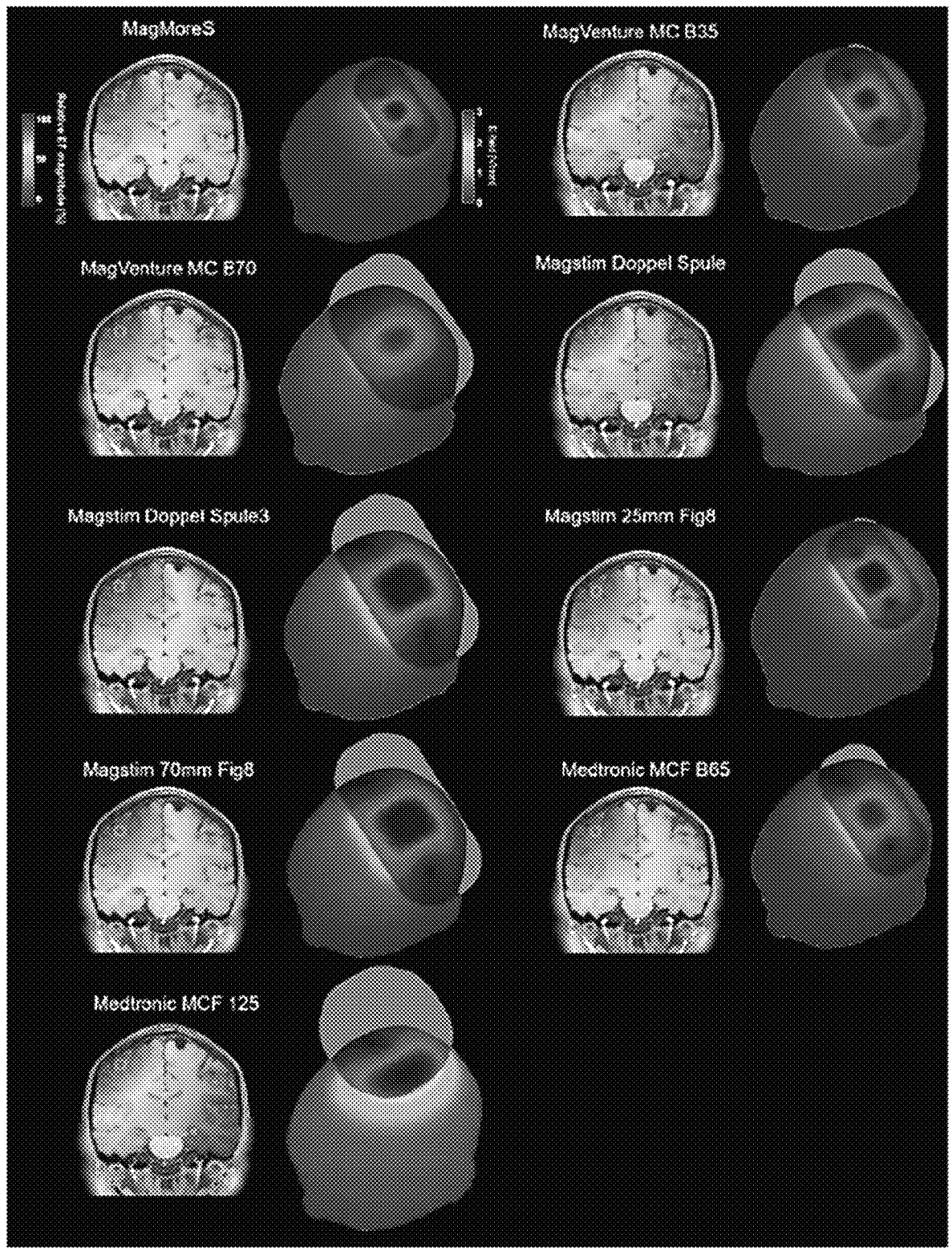
FIG. 14 is a view illustrating examples of visualizing states in which an electrical stimulus induced from a magnetic field of a treatment coil propagates in a brain of an object are illustrated.

Referring to FIG. 14, examples of visualizing states in which an electrical stimulus induced from a magnetic field of a treatment coil propagates in a brain of an object are illustrated.

In the disclosed embodiment, the computer is connected to a robot arm device provided with a TMS treatment coil. The robot arm device includes a machine device that may move the TMS treatment coil to a location designated by the computer.

The robot arm device may automatically perform a treatment using a TMS coil on a patient according to a calculation result of the computer by moving the TMS treatment coil to a location designated by the computer according to the disclosed embodiment.

Figure 15:
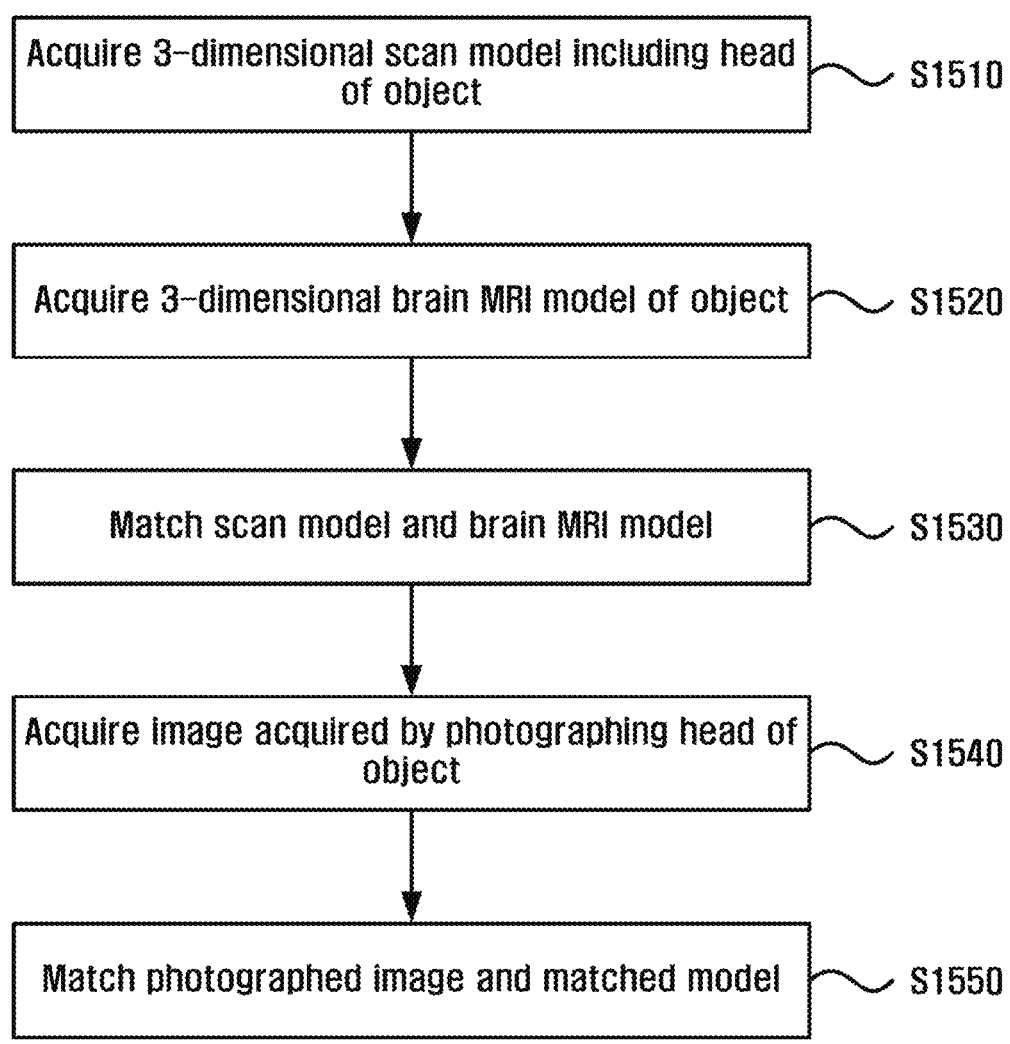
FIG. 15 is a flowchart illustrating a patch guide method according to an embodiment.

FIG. 15 is a flowchart illustrating a patch guide method according to an embodiment.

In the disclosed embodiment, a patch includes a brain stimulating patch. For example, the brain stimulating patch may include an electrical stimulation patch and an ultrasonic stimulation patch. Further, the patch includes an EEG patch. Meanwhile, the types of the patches according to the disclosed embodiment are not limited to the above-mentioned examples.

In operation S1510, the computer acquires a 3-dimensional scan model including the head of the object by using a depth camera.

The depth camera may include a 3-dimensional laser scanner of a triangulation method, a camera using a structural ray pattern, and a depth camera using a time-of-flight (TOF) method using a reflection time difference of an infrared ray.

The depth camera is used to acquire a 3-dimensional scan model by reflecting distance information on an image.

In an embodiment, an object, that is, a patient is seated on a circular chair with no back, and a user, that is, a doctor locates the depth camera such that the face of the patient is viewed well from a height of the face of the patient by using a temporary fixing device, such as, a tripod.

The doctor starts scan by using the depth camera, and acquires a 3-dimensional scan model including the head of the patient by rotating the patient slowly by one turn.

In an embodiment, the depth camera is provided in a fixing module that may be automatically rotated, and may acquire a 3-dimensional scan model as the depth camera is rotated round the patient located at the center.

Meanwhile, according to the disclosed embodiment, in order that 3-dimensional scan may be allowed without using separate high-priced equipment, the depth camera module is connected to a portable computing device (for example, a smartphone or a tablet PC), the computing device, to which the camera module is connected, is fixed by using a temporary fixing device, such as a tripod, which may be easily obtained, and a 3-dimensional scan model may be acquired by seating the patient on a stool and rotating the patient.

Figure 20:
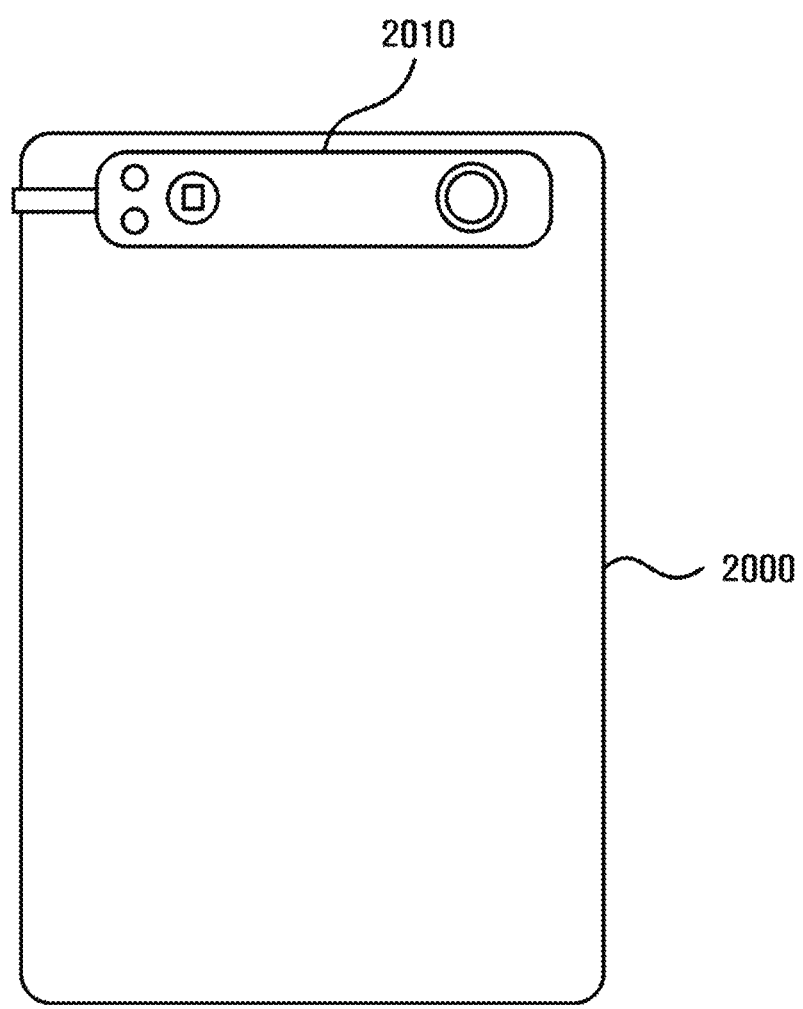
FIG. 20 is a view illustrating a portable computing device and a depth camera module connected to the portable computing device.

Referring to FIG. 20, a portable computing device 2000 and a depth camera module 2010 connected to the portable computing device 2000 are illustrated.

Figure 18:
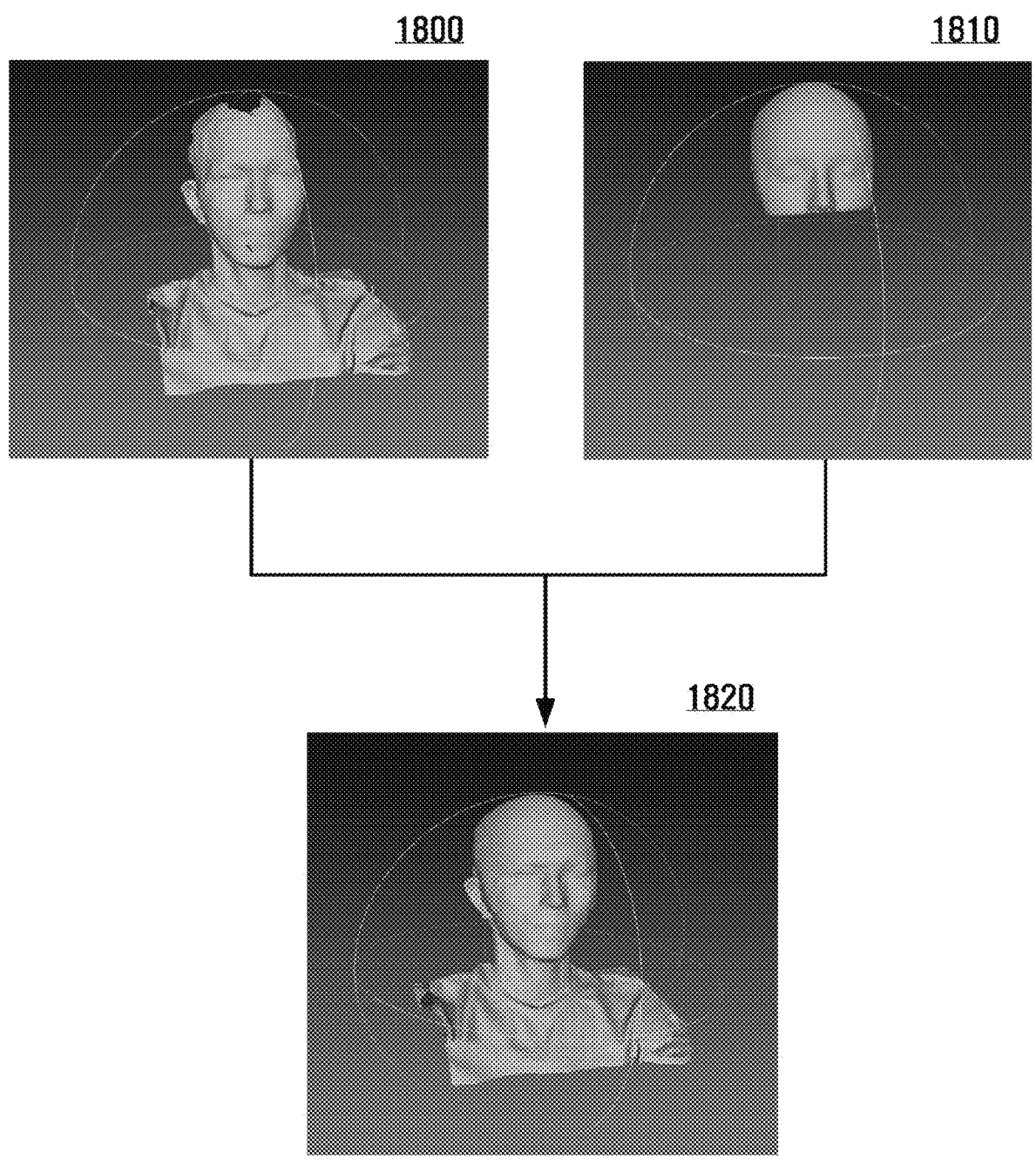
FIG. 18 is a view illustrating an example of a 3-dimensional scan model acquired by using a depth camera.

Further, referring to FIG. 18, an example of a 3-dimensional scan model 1800 acquired by using a depth camera is illustrated.

In an embodiment, the computer generates a 3-dimensional model including the head of an object by using a distance image collected by using a depth camera, and aligns images photographed at different time points and adds the images to reconstruct a 3-dimensional model of the object. For example, the computer reconstructs a model by collecting 3-dimensional data in a point cloud form in distance images collected by using the depth camera. However, the method for generating a 3-dimensional model is not limited.

In operation S1520, the computer acquires a 3-dimensional brain MRI model of the object.

In an embodiment, an operation of acquiring a 3-dimensional brain MRI model of an object includes an operation of acquiring a brain MRI image of an object, and an operation of generating a 3-dimensional brain map of the object that may simulate a delivery process of an electrical stimulus for the brain of the object based on the properties of a plurality of areas included in the brain MRI Image of the object.

Further, the operation of generating a 3-dimensional brain map of the object includes an operation of generating a 3-dimensional solid image including a plurality of meshes, by which a delivery process of an electrical stimulus for the brain of the object may be simulated.

The 3-dimensional brain map generating method described in relation to FIGS. 1 to 8 may be used as the method for acquiring a 3-dimensional brain MRI model of the object by the computer in operation S1520.

In operation S1530, the computer performs matching of the 3-dimensional scan model including the head of the object and the brain MRI model of the object.

Figure 17:
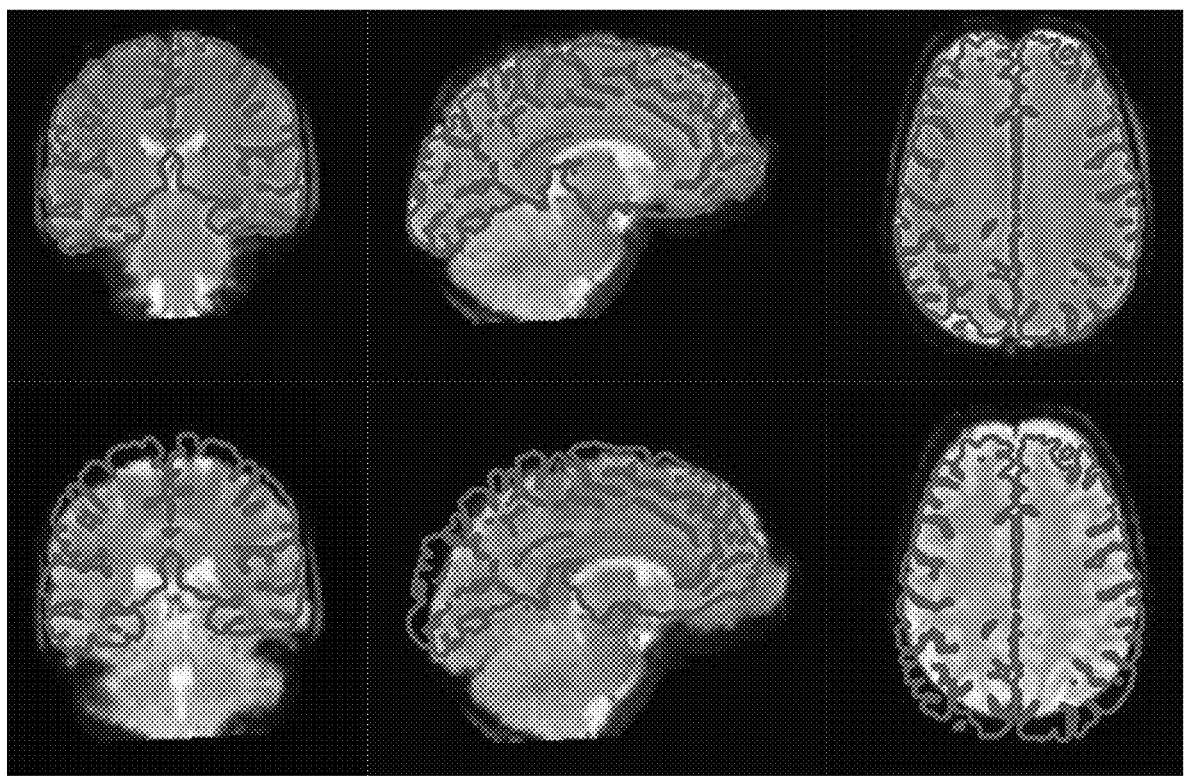
FIG. 17 is a view illustrating an embodiment of a method of matching an image.

Referring to FIG. 17, an example of matching an image is illustrated. Referring to the image 1700 illustrated in FIG. 17, a brain MRI picture of an object and an image obtained by modeling a brain structure of the object overlap each other.

In the image 1700, the lower three images correspond to an example in which the brain MRI picture and the image obtained by modeling a brain structure do not match with each other. Further, in the image 1700, the upper three images correspond to an example in which the brain MRI picture and the image obtained by modeling a brain structure do not match with each other.

The computer calculates a change generated in the brain of the object by an electrical or ultrasonic stimulus of a patch according to a location at which the patch is attached, by using a brain MRI model. Further, the computer calculates a location at which the patch is to be actually attached, by using a 3-dimensional scan model including the head of the object.

Accordingly, the computer may calculate a location at which the patch is to be attached to the head of the object by matching the 3-dimensional scan model including the head of the object and the brain MRI model of the object, and thus may calculate a change generated in the brain of the object. Similarly, the computer may calculate a location at which the patch is to be attached to the head of the object to cause a specific change in the brain of the object, and may provide the result.

In an embodiment, the operation of performing matching by the computer includes an operation of calculating a scan model and a facial feature of a brain MRI model, and an operation of matching the scan model and the brain MRI model by using the scan model and the facial feature of the brain MRI model.

The scan model including the head of the object and the brain MRI model of the object are different, and it is difficult to match them. Accordingly, the computer may match the two models by using the facial feature of the object.

In an embodiment, the operation of calculating the facial feature of the scan model including the head of the object includes an operation of acquiring a color image and a depth image including the head of the object, an operation of calculating the facial feature of the object by using a color image including the head of the object, and an operation of calculating a 3-dimensional location of the facial feature of the object by using a depth image including the head of the object.

Referring to FIG. 18, an example of generating a model 1820 that is obtained by matching the scan model 1800 including the head of the object and the brain MRI model 1810 of the object is illustrated.

In operation S1540, the computer acquires an image obtained by photographing the head of the object by using the depth camera.

For example, the doctor may move the temporarily fixed depth camera while directly carrying the depth camera such that the depth camera faces the head of the patient.

In operation S1550, one location of the image captured in operation S1540 and one location on the matched model are matched.

For example, when the computer photographs one point of the head of the object by using the depth camera, it calculates to which portion on the matched model one point being photographed corresponds.

In an embodiment, the computer matches the captured image and the matched model, and displays an image that guides the location of the patch, which is to be attached to the head of the object.

Figure 19:
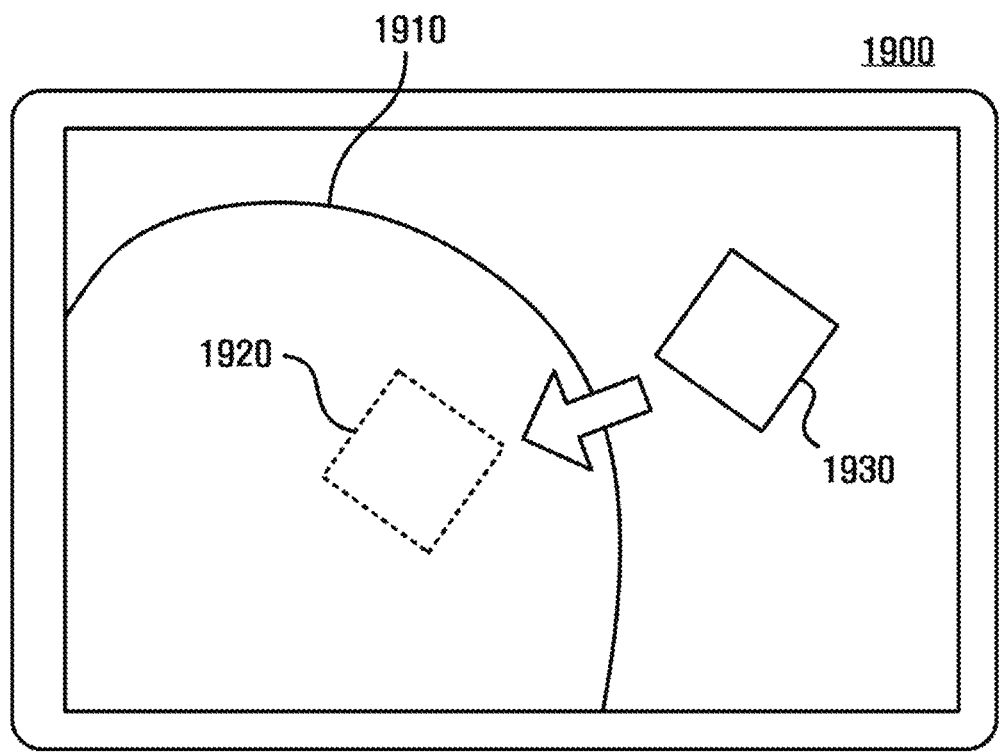
FIG. 19 is a view illustrating an example of photographing the head of an object by a computing device, to which a camera module is connected, and guiding a location at which a patch is attached to the photographed head of the object.

Referring to FIG. 19, the computing device 1900, to which the depth camera module is connected, photographs the head 1910 of the object, and the computing device 1900 displays an image that guides the location 1920 for attaching the patch 1930 to the photographed head 1910 of the head 1910.

In an embodiment, the computing device 1900 determines a location at which the patch 1930 is to be attached on the matched model, and displays a location 1920 corresponding to a location determined in the captured image.

Further, the computing device 1900 recognizes a patch 1930 in the captured image, and guides a movement direction of the recognized patch 1930.

Further, the computing device 1900 determines whether the recognized patch 1930 has been attached to the determined location 1920.

In an embodiment, at least one marker is attached to or displayed on the patch 1930. For example, at least one of a specific figure, a specific color, and a 2-dimensional code is attached to or displayed on the patch 1930, and the computing device 1900 recognizes the patch by using the marker attached to or displayed on the patch 1930 and tracks the movement of the patch 1930.

For example, when the doctor photographs the head of the patient while changing the location of the head by using the computing device 1900 or the depth camera connected to the computing device 1900, the location of the head of the patient displayed on the computing device 1900 is also changed and the location of the patch 1930 recognized by the computing device 1900 is also changed. In this case, the computing device 1900 tracks the patch 1930 even when the computing device 1900 is moved so that the doctor guides the patch 1930 such that the patch 1930 may be attached to an accurate location of the head of the patient.

In an embodiment, the computing device 1900 recognizes the patch 1930 in the captured image, and guides a movement direction of the recognized patch 1930. For example, the computing device 1900 displays a movement direction of the patch 1930 so that the patch 1930 may be attached to the determined location 1920.

Further, the computing device 1900 determines whether the recognized patch 1930 has been attached to the determined location 1920. For example, the computing device 1900 may determine whether the location finally recognized by the patch 1930 corresponds to the determined location 1920, and when the determined location 1920 and the location at which the patch 1930 is attached are different, the computing device 1900 may provide an alarm that requests change of the location of the patch 1930.

In an embodiment, the computing device 1900 recognizes the patch 1930 attached to the head of the object in the captured image, and guides the location of the recognized patch 1930. The computing device 1900 acquires a location on the matched model, which corresponds to the determined location of the patch 1930.

For example, when an EEG brain wave inspection is performed, an EEG patch is attached to a specific location regardless of the shape and structure of the head of the user or an EEG patch is attached to an arbitrary location. In this case, it is difficult to know from which direction of the brain of the object the brain wave acquired by the EEG patch has been received.

Accordingly, according to the disclosed embodiment, the computing device 1900 photographs the head of the object, to which at least one EEG patch is attached, and acquire the locations of the one or more recognized EEG patches from the captured image.

The computing device 1900 may acquire a location on the matched model of the object corresponding to the acquired location of the EEG patch, and may determine from which portion of the bran of the object the brain wave acquired by the EEG patch attached to the head of the object has been received. For example, the computing device 1900 may analyze signal sources of the brain waves received from the EEG patches by utilizing the disclosed embodiment.

Figure 16:
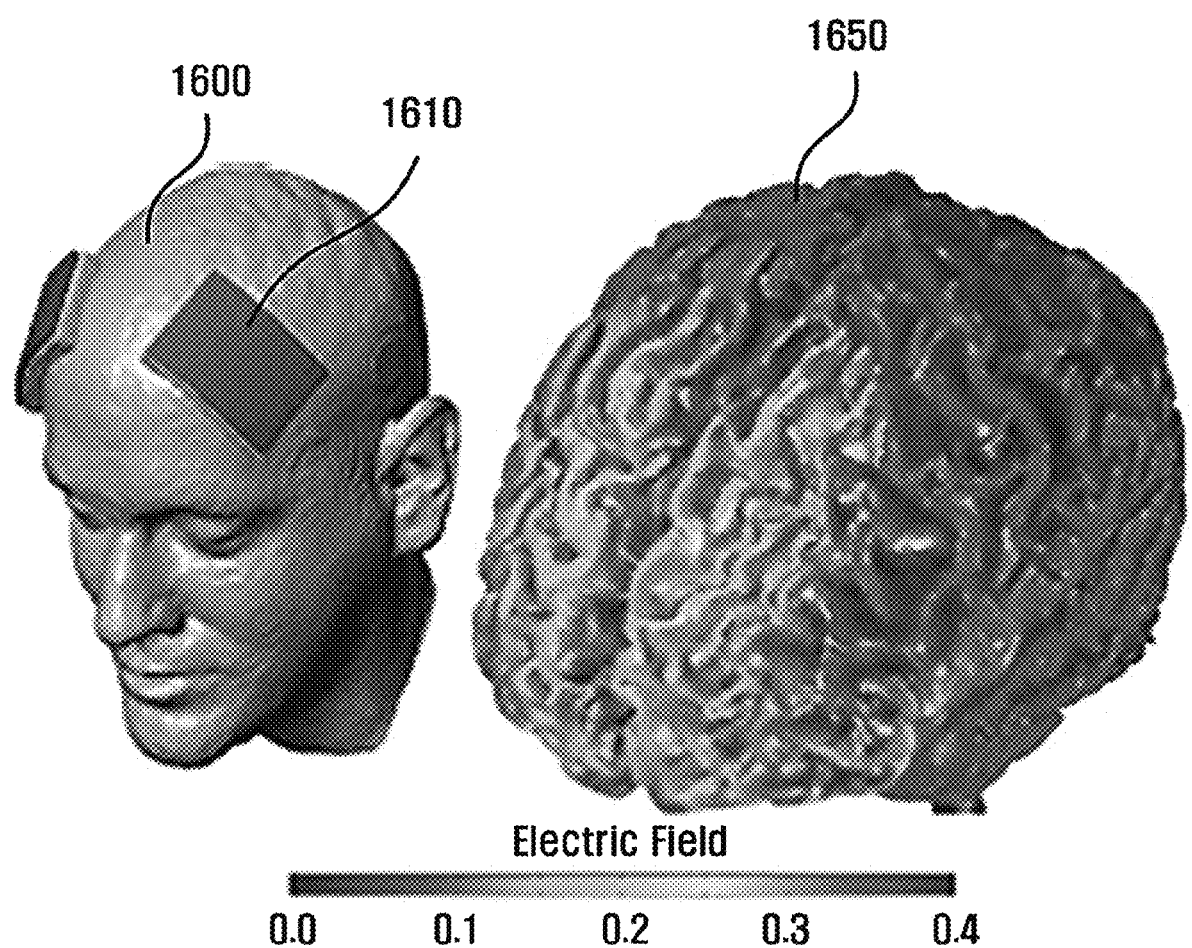
FIG. 16 is a view illustrating a result of simulating an electrical stimulation result according to an embodiment.

FIG. 16 is a view illustrating a result of simulating an electrical stimulation result according to an embodiment.

Referring to FIG. 16, a 3-dimensional model of the head 1600 of an object and an embodiment in which the patch 1610 is attached to one location on the 3-dimensional model are illustrated.

When the patch 1610 is attached to one location of the 3-dimensional model of the head 1600 of the object, the computer simulates a result in which the electrical stimulus by the patch 1610 is delivered to the brain 1650.

In an embodiment, the computer acquires a 3-dimensional brain map for the brain 1650 of the object, and determines the location of the patch 1610, which is to be attached to the head of the object, by using the 3-dimensional brain map.

In an embodiment, the operation of determining a location of the patch includes an operation of acquiring an objective of using the patch 1610, an operation of simulating a process of delivering an electrical stimulus to the brain 1650 of the object according the location at which the patch 1610 is attached to the head 1600 of the object, and an operation of determining the location of the patch 1610 by using the acquired object and the simulation result.

When a specific stimulus is to be applied to the brain 1650 of the object, the computer may determine a location of the patch 1610 at which a specific stimulus may be applied to the brain 1650 of the object by using the simulation result.

The computer may match the location of the patch 1610 determined according to the embodiment illustrated in FIG. 16 with one point of the head of the object photographed by using the depth camera, and may display an image that guides the patch to the matched location.

The steps of a method or an algorithm that have been described in relation to the embodiments of the inventive concept may be directly implemented by hardware, may be implemented by a software module executed by hardware, or may be implemented by a combination thereof. The software module may reside in a random access memory (RAM), a read only memory (ROM), an erasable programmable ROM (EPROM), an electrically erasable programmable ROM (EEPROM), a flash memory, a hard disk, a detachable disk, a CD-ROM, or a computer readable recording medium in an arbitrary form, which is well known in the art to which the inventive concept pertains.

According to the disclosed embodiment, the brain MRI image may be automatically segmented in a short time by segmenting the brain MRI image by utilizing a model learned in advance.

Accordingly, the 3-dimensional brain image may be acquired by any one in a short time in the medical field, and a simulation result, by which the effect of an electrical stimulus to the brain of the object may be visually identified, may be provided.

Further, by guiding the location of the patch by using head modeling and MRI modeling, the location of the patch in consideration of different heads and brain structures of people may be guided.

Further, a more accurate result may be obtained through the EEG brain wave inspection by determining the location of the EEG patch by using head modeling and MRI modeling.

The aspect of the inventive concept is not limited thereto, and other unmentioned aspects of the inventive concept may be clearly appreciated by those skilled in the art from the following descriptions.

Although the exemplary embodiments of the inventive concept have been described with reference to the accompanying drawings, it will be understood by those skilled in the art to which the inventive concept pertains that the inventive concept can be carried out in other detailed forms without changing the technical spirits and essential features thereof. Therefore, the above-described embodiments are exemplary in all aspects, and should be construed not to be restrictive.

What is claimed is:

1. A patch guide method comprising:
   acquiring a 3-dimensional scan model including the head of an object by using a depth camera, by a computer;
   acquiring a 3-dimensional brain MRI model of the object;
   matching the 3-dimensional scan model and the 3-dimensional brain MRI model to acquire a matched model;
   acquiring an image captured by photographing the head of the object by using the depth camera;
   matching one location in the captured image and one location on the matched model; and
   determining a location of at least one patch configured to be attached to the head of the object, by using a 3-dimensional brain map,
   wherein the acquiring of the 3-dimensional brain MRI model of the object includes:
      acquiring a brain MRI image of the object;
      acquiring physical characteristics of a plurality of areas included in the brain MRI image, the physical characteristics including isotropic electrical conductivities of the plurality of areas and/or anisotropic electrical conductivities of the plurality of areas; and
      generating the 3-dimensional brain map of the object based on the acquired physical characteristics of the plurality of areas included in the brain MRI image, and
   wherein the determining the location of the at least one patch includes:
      acquiring a target stimulus point, to which an electrical stimulus is to be applied in a brain of the object, by using the 3-dimensional brain map, wherein the electrical stimulus is applied by using an electric field induced in the brain of the object with a magnetic field generated by a treatment coil;
      acquiring information on spatial distribution of magnetic vector potentials of the treatment coil based on a shape of the treatment coil;
      acquiring an optimal stimulus condition, in which an intensity of the magnetic field applied to the target stimulus point is maximized by the treatment coil, based on the information on the spatial distribution;
      performing a simulation of a delivery process of the electrical stimulus to the target stimulus point with the optimal stimulus condition; and
      determining the location of the at least one patch by using a result of the simulation.

2. The patch guide method of claim 1, wherein the determining comprises:
   recognizing the at least one patch included in the captured image;
   determining the location of the at least one patch in the captured image; and
   acquiring the one location on the matched model corresponding to the location of the at least one patch.

3. The patch guide method of claim 1, wherein the matching of the 3-dimensional scan model and the 3-dimensional brain MRI model includes:
   calculating facial features of the object in the 3-dimensional scan model and the 3-dimensional brain MRI model; and
   matching the 3-dimensional scan model and the 3-dimensional brain MRI model by using the facial features of the object in the 3-dimensional scan model and the 3-dimensional brain MRI model.

4. The patch guide method of claim 3, wherein the calculating of the facial features of the object comprises:
   acquiring a color image and a depth image including the head of the object;
   calculating the facial features of the object by using the color image; and
   calculating a 3-dimensional location of the facial features of the object by using the depth image.

5. The patch guide method of claim 1, further comprising:
   displaying the captured image showing the location of the at least one patch configured to be attached to the head of the object,
   wherein
   the location of the at least one patch is determined on the matched model.

6. The patch guide method of claim 5, further comprising:
   recognizing the at least one patch included in the captured image;
   guiding a movement direction of the at least one patch; and
   determining whether the at least one patch is attached at the determined location.

7. The patch guide method of claim 1, wherein the generating of the 3-dimensional brain map includes:
   generating the 3-dimensional brain map constituted by a plurality of meshes by performing the simulation of the delivery process.

8. A non-transitory computer-readable recording medium storing a program, and configured to be coupled to a computer being hardware, the program include instructions to execute the method of claim 1.

9. The patch guide method of claim 1, wherein the acquiring the physical characteristics comprise acquiring the isotropic electrical conductivities by allocating predetermined electrical conductivities to respective areas of the plurality of areas.

10. The patch guide method of claim 1, wherein the acquiring the physical characteristics comprise acquiring the anisotropic electrical conductivities based on anisotropy of white matter fibers in a white matter of the brain.

11. The patch guide method of claim 1, wherein the acquiring the physical characteristics comprise acquiring the anisotropic electrical conductivities from a conductive tensor image for the brain of the object.

12. The patch guide method of claim 1, wherein the acquiring the physical characteristics comprise acquiring the anisotropic electrical conductivities from a diffusion tensor image for the brain of the object.

* * * * *